US006784309B2

(12) United States Patent
Prakash et al.

(10) Patent No.: US 6,784,309 B2
(45) Date of Patent: *Aug. 31, 2004

(54) METHOD FOR THE PURIFICATION OF N-[N-(3,3-DIMETHYLBUTYL)-L-α-ASPARTYL]-L-PHENYLALANINE 1-METHYL ESTER

(75) Inventors: Indra Prakash, Hoffman Estates, IL (US); Kurt Wachholder, Palatine, IL (US)

(73) Assignee: The Nutrasweet Company, Chicago, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/550,316

(22) Filed: Apr. 14, 2000

(65) Prior Publication Data

US 2002/0038046 A1 Mar. 28, 2002

Related U.S. Application Data

(60) Provisional application No. 60/145,935, filed on Jul. 28, 1999.

(51) Int. Cl.[7] ............................................. C07C 229/00
(52) U.S. Cl. .......................................... 560/40; 560/41
(58) Field of Search ....................................... 560/40, 41

(56) References Cited

U.S. PATENT DOCUMENTS

| 5,480,668 A | 1/1996 | Nofre et al. ................. 426/548 |
| 5,510,508 A | 4/1996 | Claude et al. ................. 560/41 |
| 5,728,862 A | 3/1998 | Prakash ....................... 560/40 |

FOREIGN PATENT DOCUMENTS

WO            99/58554         11/1999

OTHER PUBLICATIONS

Derwent abstract (Acc No. 1999–244007) of JP 11080108. Takemoto (1999). Purifying N–[N–(3,3–dimethylbutyl-)–L–a–aspartyl]–L–phenylalanine 1–methyl ester, by two phase solvent extraction.*

Caplus abstract (1999:206867) of JP 1180108. Takemoto (1999). Purification and recovery of N–[N–(3,3–dimethylbutyl)–L–a–aspartyl]–L–phenylalanine 1–methyl ester as sweetener.*

* cited by examiner

Primary Examiner—Ralph Gitomer
(74) Attorney, Agent, or Firm—Jeffrey M Hoster; Fitzpatrick, Cella, Harper & Scinto

(57) ABSTRACT

This invention relates to the purification of N-[N-(3,3-dimethylbutyl)-L-α-aspartyl]-L-phenylalanine 1-methyl ester by slurrying a mixture containing N-[N-(3,3-dimethylbutyl)-L-α-aspartyl]-L-phenylalanine 1-methyl ester with organic or aqueous organic solvents.

7 Claims, 2 Drawing Sheets

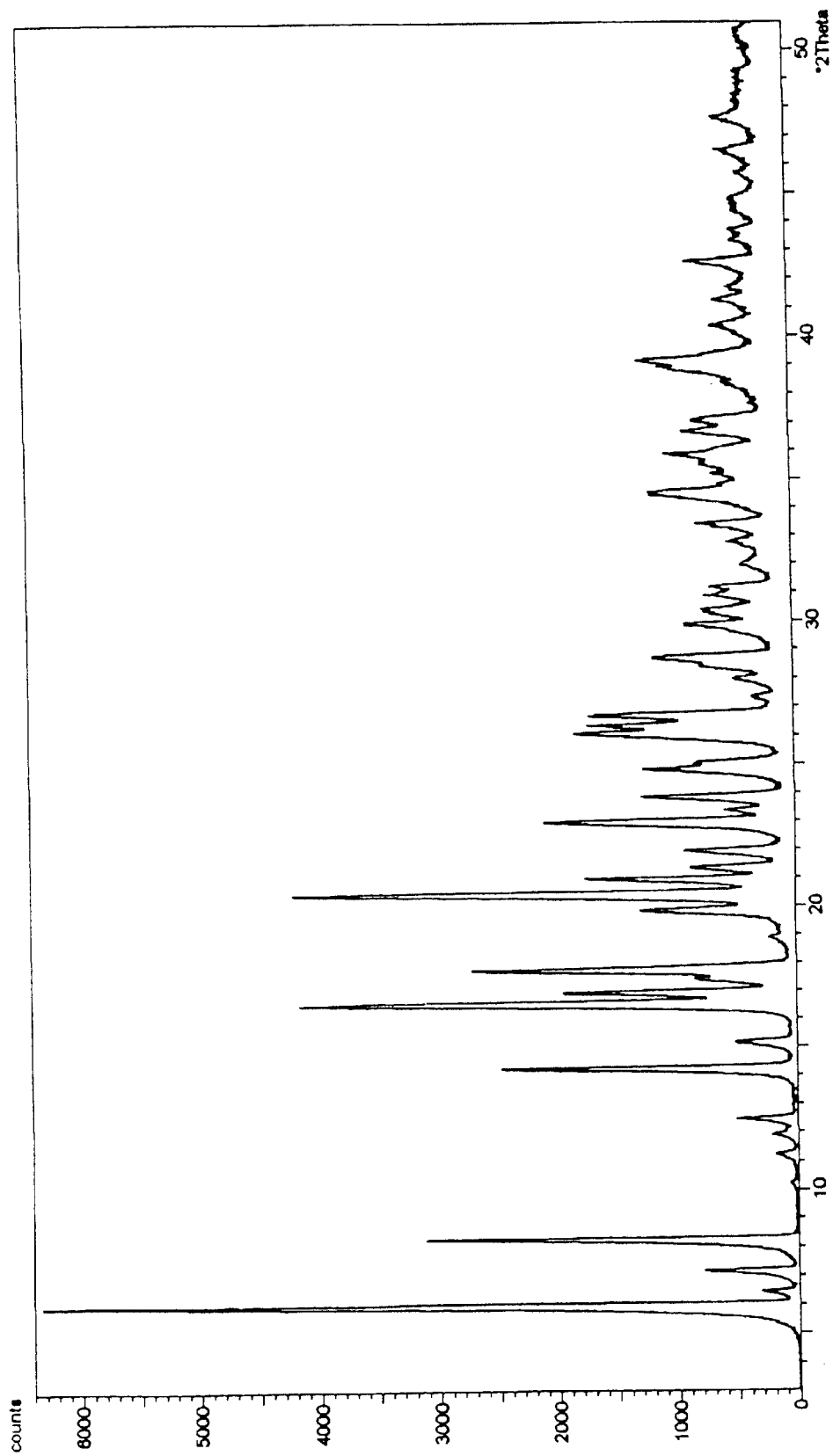
Figure 1. Powder X-ray Pattern of L,L-α-Neotame (from MTBE/Water)

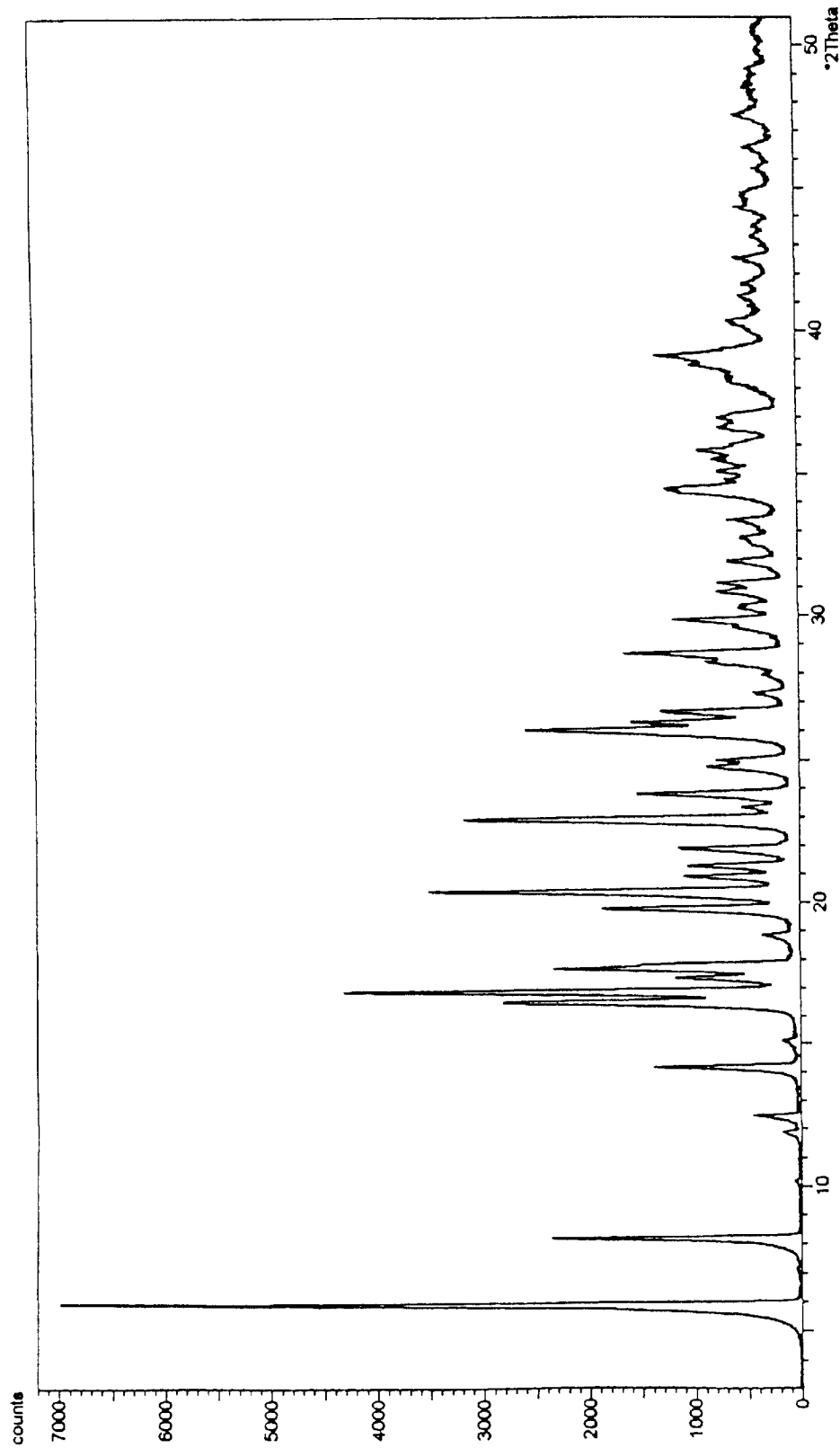
Figure 2. Powder X-ray Pattern of L,L-α-Neotame (from Ethyl Acetate)

METHOD FOR THE PURIFICATION OF N-[N-(3,3-DIMETHYLBUTYL)-L-α-ASPARTYL]-L-PHENYLALANINE 1-METHYL ESTER

This application claims the benefit of U.S. Provisional Patent application Ser. No. 60/145,935, filed Jul. 28, 1999.

BACKGROUND OF THE INVENTION

1. Field of the Invention

This invention relates to an improved method for purification of an N-alkylated aspartame derivative, which is a particularly useful sweetening agent.

2. Related Background Art

N-[N-(3,3-dimethylbutyl)-L-α-aspartyl]-L-phenylalanine 1-methyl ester (neotame) is a high potency dipeptide sweetener (about 8000X sweeter than sucrose) that has the formula

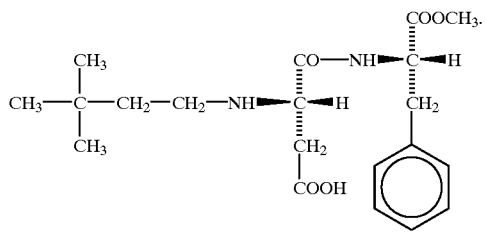

The synthesis of neotame is disclosed in U.S. Pat. No. 5,480,668, U.S. Pat. No. 5,510,508 and U.S. Pat. No. 5,728,862, the disclosure of each of which is incorporated by reference herein. These processes, however, may produce several impurities, including N,N-di(3,3-dimethylbutyl)-L-aspartyl-L-phenylalanine methyl ester (dialkylated aspartame), α-methyl hydrogen-3-(3,3-dimethylbutyl)-2-L-(2,2-dimethylpropyl)-5-oxo-α-L-(phenylmethyl)-1,4(L)-imidazolidine diacetate (dialkylated imidazolidinone), N-[N-(3,3-dimethylbutyl)-L-α-aspartyl]-L-phenylalanine (demethylated α- or β-neotame) and methyl ester of N-[N-(3,3-dimethylbutyl)-L-α-aspartyl]-L-phenylalanine 1-methyl ester (methylated α- or β-neotame). These impurities are represented respectively by the structural formulae:

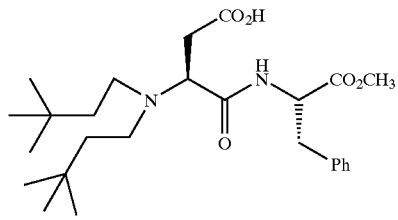

dialkylated aspartame

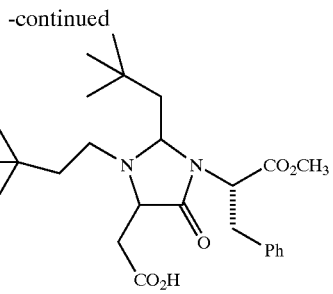

dialkylated imidazolidinone

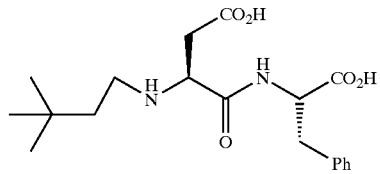

demethylated α-neotame

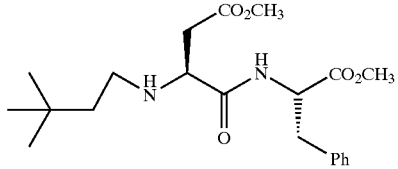

methylated α-neotame

The primary impurities generated in the synthesis of N-[N-(3,3-dimethylbutyl)-L-α-aspartyl]-L-phenylalanine 1-methyl ester, i.e., dialkylated aspartame, methyl ester of α-neotame and dialkylated imidazolidinone, have very similar solubilities compared to N-[N-(3,3-dimethylbutyl)-L-α-aspartyl]-L-phenylalanine 1-methyl ester and thus are difficult to remove by crystallization, thereby making it difficult to obtain pure product in high yield.

Since neotame is mainly employed in foods for human consumption, it is extremely important that neotame exist in a highly purified state. Thus, it is clear that there is a need to economically produce pure N-[N-(3,3-dimethylbutyl)-L-α-aspartyl]-L-phenylalanine 1-methyl ester.

SUMMARY OF THE INVENTION

This invention is directed to a process of purifying [N-(3,3-dimethylbutyl)-L-α-aspartyl]-L-phenylalanine 1-methyl ester. The process comprises the steps of: (a) washing neotame with water; (b) combining the water washed neotame with an organic solvent to form a slurry; and (c) filtering the slurry to recover purified neotame. The organic solvent of step (b) may be an aqueous organic solvent.

Preferably, the process includes the steps of washing the neotame recovered in step (c) with an organic solvent, which may be the same or different than the organic solvent of step (b) and drying the washed filtered slurry to recover further purified neotame.

BRIEF DESCRIPTION OF THE DRAWINGS

FIGS. 1 and 2 are the powder x-ray diffraction patterns of the purified neotame obtained by the methods of Examples 1 and 2, respectively.

DETAILED DESCRIPTION OF THE INVENTION

The aforementioned process purifies by removing dialkylated aspartame, methylated α-neotame, demethylated α-neotame, demethylated β-neotame, aspartame and dialkylated imidazolidinone impurities from neotame from post-hydrogenation mixtures or from mother liquors of crystallized neotame.

As described herein the step of washing neotame with water can be carried out in any way that allows for the contact of neotame with water. The water may contain water miscible solvents, e.g. alcohols, acetonitrile, acetone and the like, in an amount up to about 5–15% by weight. The water wash can be achieved for example, by adding solid neotame to the water, or adding water to an organic solvent solution of neotame and then drying off the organic solvent. The wash may be a batch wash, continuous wash, or the like. For example, the solid neotame may be stirred with water and filtered. This step of the process reduces demethylated α-neotame and demethylated β-neotame, which are more soluble in water compared to neotame.

Generally, the water wash is conducted at a temperature in a range of about 10° C. to about 50° C. for a time of about 0.5 to about 30 hours. After the water wash, the neotame is typically separated from the water by filtration or centrifugation. If desired the recovered neotame may be dried in a vacuum oven, tumble dryer, or cone dryer at a temperature of about 25°–50° C.

The slurry of neotame and organic solvent is formed by combining the solvent and neotame in any desirable manner for a specific time. It is preferable to stir the mixture. Typically, the mixture is held at a temperature of about 15° C. to about 45° C. for a time of about 0.5 to about 30 hours. The slurry is then filtered or centrifuged to recover the purified neotame.

If desired a second slurry may be formed using the same or different organic solvent followed by filtration or centrifugation. The recovered neotame is then preferably dried at a temperature of about 30° C.–50° C. and a pressure of about 10–250 mm Hg.

Exemplary organic solvents employed in the process of this invention include ethyl acetate, diethyl ether, tert butyl methyl ether, butyl acetate, methyl acetate, propyl acetate, isopropyl acetate, cyclohexane, hexane, heptane, pentane, acetone, acetonitrile, methanol, ethanol, isopropanol, butanol, dichloromethane or chloroform. Preferably the organic solvents employed are tert butyl methyl ether or ethyl acetate.

As previously noted the water washed N-[N-(3,3-dimethylbutyl)-L-α-aspartyl]-L-phenylalanine 1-methyl ester may be slurried with an aqueous organic solvent. Other organic solvents that may be used in the process of this invention include, without limitation: tert butyl methyl ether (MTBE), diethylether, acetone/hexane, acetonitrile/hexane, acetonitrile/heptane, acetonitrile/pentane, methanol/heptane, ethanol/hexane, isopropanol/hexane, methanol/hexane, butanol/hexane, dichloromethane/hexane or chloroform/hexane.

Preferably, the N-[N-(3,3-dimethylbutyl)-L-α-aspartyl]-L-phenylalanine 1-methyl ester starting material purified by the process of this invention is obtained using the techniques and procedures described in U.S. Pat. No. 5,510,508, U.S. Pat. No. 5,480,668 U.S. Pat. No. 5,782,862 and in co-pending application, U.S. Provisional appln. Ser. No. 60/110,011, the disclosures of each of which are incorporated by reference herein.

A preferred embodiment of this invention is directed to a process of purifying N-[N-(3,3-dimethylbutyl)-L-α-aspartyl]-L-phenylalanine 1-methyl ester (neotame) by a process comprising the steps of (i) filtering an organic solvent preferably a methanol solution containing N-[N-(3,3-dimethylbutyl)-L-α-aspartyl]-L-phenylalanine 1-methyl ester to create a filtrate; (ii) adding water to the filtrate; (iii) removing the organic solvent from the filtrate to precipitate solids, preferably under reduced pressure with stirring; (iv) filtering the precipitated solid; (v) washing the precipitated solid with water and drying to obtain water-washed neotame; (vi) mixing the water-washed neotame with an organic solvent, which may be the same or different than the organic solvent of step (i) to create a slurry; (vii) filtering the slurry; (viii) washing the filtered slurry with an organic solvent which may be the same or different than the organic solvent of step (vi); and (ix) drying the slurry to obtain purified neotame.

As used herein, the term "solution" refers to any N-[N-(3,3-dimethylbutyl)-L-α-aspartyl]-L-phenylalanine 1-methyl ester-containing solution. This includes, without limitation, hydrogenation reaction mixtures, crystallization mother liquors, wash liquors and waste streams.

EXAMPLE 1

The hydrogenation mixture (120 mL) containing 10% (by wt.) of neotame in methanol was filtered through a one inch celite bed on a sintered glass funnel. Water (60 mL) was added to the filtrate and methanol was removed under reduced pressure at 35° to 40° C. The mixture was stirred at room temperature for 2–16 hours. The precipitated solid was filtered, washed with water (100 ml) and dried at 35° to 40° C. for 16–24 hours to get 80–85% of crude neotame. This product had 7% of impurities (dialkylated aspartame, methylated α-neotame, demethylated α-neotame and dialkylated imidazolidinone). Ten grams of crude neotame was stirred with 80 mL of tert butyl methyl ether (MTBE) at 22°–26° C. for 1 hour. The slurry was filtered, washed with 20 mL of MTBE and 50 mL of water, and dried at 37°–40° C. for 12–24 hours to get 8.8–9.1 g of pure neotame. This product had a total of about 0.1% wt/wt of dialkylated aspartame, methylated α-neotame, demethylated α-neotame and dialkylated imidazolidinone by HPLC. FIG. 1 shows the powder x-ray pattern of the purified neotame obtained through this method.

EXAMPLE 2

The hydrogenation mixture (120 mL) was filtered through a one inch celite bed on a sintered glass funnel. Water (60 mL) was added to the filtrate and methanol was removed under evaporated under reduced pressure at 35°–40° C. The mixture was stirred at room temperature for 4–16 hours. The precipated solid was filtered, washed with water and dried at 35°–40° C. for 16–24 hours to get 80–85% of crude neotame. This product contained ~10% impurities (dialkylated aspartame, methylated α-neotame and dialkylated imidazolidinone). Ten grams of crude neotame was stirred with 14 mL of ethyl acetate at 22°–26° C. for 2 hours. The slurry was filtered and washed with water (10 mL). The wet product was dried at 40°–45° C. for 12–24 hours to get 6.8 g of pure neotame. This product had a total of 0.2% of dialkylated neotame, methylated α-neotame, and dialkylated imidazolidinone by HPLC. FIG. 2 shows the powder x-ray pattern of the purified neotame obtained through this method.

Other variations or modifications, which will be obvious to those skilled in the art, are within the scope and teachings of this invention. This invention is not to be limited except as set forth in the following claims.

We claim:

1. A process for purifying N-[N-(3,3-dimethylbutyl)-L-α-aspartyl]-L-phenylalanine 1-methyl ester comprising the steps of:
   (a) washing N-[N-(3,3-dimethylbutyl)-L-α-aspartyl]-L-phenylalanine 1-methyl ester with water;
   (b) recovering by filtration the water washed N-[N-(3,3-dimethylbutyl)-L-α-aspartyl]-L-phenylalanine 1-methyl ester in solid form;
   (c) combining the recovered N-[N-(3,3-dimethylbutyl)-L-α-aspartyl]-L-phenylalanine 1-methyl ester with an organic solvent to form a slurry;
   (d) recovering by filtration N-[N-(3,3-dimethylbutyl)-L-α-aspartyl]-L-phenylalanine 1-methyl ester from the slurry in solid form; and
   (e) washing said recovered N-[N-(3,3-dimethylbutyl)-L-α-aspartyl]-L-phenylalanine 1-methyl ester with water and organic solvent.

2. The process according to claim 1, wherein the water wash is conducted at a temperature of about 10° C. to about 50° C.

3. The process according to claim 1, wherein the water wash is conducted for a time of about 0.5 to about 30 hours.

4. The process according to claim 1, wherein the slurry is held at a temperature of about 15° C. to about 45° C.

5. The process according to claim 1, wherein the slurry is held for a time of about 0.5 to about 30 hours.

6. The process according to claim 1, wherein said organic solvent of step (c) is selected from the group consisting of tert butyl methyl ether, ethyl acetate, diethyl ether, methyl acetate, butyl acetate, propyl acetate, isopropyl acetate, cyclohexane, acetone, acetonitrile, heptane, pentane, dichloromethane, chloroform and mixtures thereof.

7. The process according to claim 1, wherein said organic solvent of step (c) is a mixture of organic solvents selected from the group consisting of acetone/hexane, acetonitrile/hexane, acetonitrile/heptane, acetonitrile/pentane, ethanol/hexane, methanol/hexane, methanol/heptane, isopropanol/hexane, butanol/hexane, dichloromethane/hexane, and chloroform/hexane.

* * * * *